United States Patent
Brown et al.

(10) Patent No.: US 9,606,061 B2
(45) Date of Patent: *Mar. 28, 2017

(54) SYSTEM AND METHOD FOR PH FORMULATIONS

(71) Applicant: Unchained Labs, Pleasanton, CA (US)

(72) Inventors: Richard Brown, East Falmouth, MA (US); Burleigh Hutchins, West Brookfield, MA (US); Ernesto Freire, North Bethesda, MD (US)

(73) Assignee: Unchained Labs, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,666

(22) Filed: May 12, 2015

(65) Prior Publication Data

US 2015/0241354 A1    Aug. 27, 2015

Related U.S. Application Data

(62) Division of application No. 13/214,353, filed on Aug. 22, 2011, now abandoned.

(60) Provisional application No. 61/375,920, filed on Aug. 23, 2010.

(51) Int. Cl.
| | |
|---|---|
| *G01N 21/76* | (2006.01) |
| *G01N 21/64* | (2006.01) |
| *G01N 1/38* | (2006.01) |
| *G01N 33/68* | (2006.01) |
| *G01N 35/10* | (2006.01) |

(52) U.S. Cl.
CPC .......... *G01N 21/6486* (2013.01); *G01N 1/38* (2013.01); *G01N 33/6803* (2013.01); *G01N 35/1065* (2013.01); *G01N 35/1072* (2013.01)

(58) Field of Classification Search
None
See application file for complete search history.

(56) References Cited

U.S. PATENT DOCUMENTS

| | | |
|---|---|---|
| 5,132,916 A | 7/1992 | Gulaian et al. |
| 6,232,085 B1 | 5/2001 | Pantoliano et al. |
| 2004/0157266 A1 | 8/2004 | Oas et al. |
| 2009/0298186 A1 | 12/2009 | Brigham-Burke et al. |

OTHER PUBLICATIONS

International Search Report/Written Opinion mailed Apr. 9, 2012 in PCT application No. PCT/US2011/048799.
Park, et al. "Analysis of the m-value Change in the Equilibrium Unfolding of Hydrophobic Core Variant Ubiquitin", *Journal of the Korean Chemical Society*, 2005, vol. 49, No. 5, pp. 479-487.
Quick Optimize, 1991, Hampton Research, retrieved from internet: http://hamptonresearch.com/documents/product!hr003414_2-223_user_guide.pdf.

*Primary Examiner* — Robert Xu
(74) *Attorney, Agent, or Firm* — Cooley LLP; Matthew Pavao (57) ABSTRACT

A system and method for creating a buffer solution having a desired pH value is disclosed. The method uses two known buffer solutions, each with predetermined pH values, and determines a mathematical relationship which defines the amount of each known buffer solution needed to create the buffer solution with the desired pH. This method can then be used to create one or more denaturation graphs, which demonstrate the stability of a protein at a given pH level.

5 Claims, 9 Drawing Sheets

SYSTEM AND METHOD FOR PH FORMULATIONS

This application is a divisional of U.S. patent application Ser. No. 13/214,353, which claims priority from U.S. Provisional Patent Application Ser. No. 61/375,920, filed Aug. 23, 2010, the disclosures of which are incorporated herein by reference in their entireties.

BACKGROUND OF THE INVENTION

Protein therapeutics is the fastest growing segment of the biotechnology and pharmaceutical industry. Protein therapeutics includes monoclonal antibodies, recombinant proteins, chimeric proteins and other protein receptor constructs. This segment is expected to reach over $70 billion in sales by 2011.

A major hurdle in the development and use of proteins as pharmaceutical drugs is the ability to store, transport and deliver them in a safe stable form. It is well known that factors, such as temperature, solvent, ligands, excipients, pH, and salt concentration, affect a particular protein's stability. The identification of buffer, ligand and excipient conditions that maximize the stability and eliminate protein aggregation is critical during development and often requires the evaluation of hundreds of conditions. This combination of buffer, ligand and excipients conditions is referred to as the storage formulation throughout this disclosure. Unfortunately, it is difficult to vary all of the various parameters to determine the ideal storage formulation for a particular protein.

There are different ways to measure protein stability and each involves disrupting the protein structure through either physical or chemical means. This disruption of the protein structure is referred to as denaturation.

Temperature is one of the most widely used physical denaturants. In this scenario, a protein is subjected to increasing temperature and the corresponding changes in its structure are recorded. One of the disadvantages of temperature denaturation is that proteins typically denature at temperatures at or above 60° C. However, in most instances, the temperatures of interest are physiological (about 37° C.), room (about 25° C.) and storage (4° C.). Thus, results from temperature-based denaturation tests must be extrapolated by more than 25° C. to understand the effects at the temperatures of interest. In addition, most proteins used as biologics undergo irreversible temperature denaturation, which precludes a meaningful calculation of thermodynamic stability at the temperatures of interest. Also, a formulation that elicits a higher denaturation temperature does not necessarily result in a more stable protein at room temperature.

A second way to measure protein stability is through the use of chemical denaturants, such as urea or guanidine hydrochloride. This method permits measurements to be done at any desired temperature.

The structural stability of a protein is determined by its Gibbs energy of stability, $\Delta G$. This value, $\Delta G$, is a function of temperature, chemical denaturants and other physical and chemical variables. Using the common example of a two state model, where a protein is either folded (i.e. native) or unfolded (i.e. denatured), the protein can transition between these two states:

N⇔, wherein N is the native (folded) state and
U is the unfolded state.

Two different rate constants can be defined from this transitional equation. $K_f$ is the rate of the folding reaction, while $K_u$ is the rate of the unfolding reaction. Finally, the equilibrium constant, K, can be defined as the ratio of the unfolding rate to the folding rate, or $$K = \frac{K_u}{K_f}.$$

Furthermore, the Gibbs energy can be expressed in terms of K, as $$\Delta G = -RT \ln(K),$$

where R is the gas constant, T is the temperature, expressed in Kelvin and ln(K) is the natural log of K. Thus, if K is greater than one, the protein unfolds at a higher rate than it folds, and its Gibbs energy is negative. Conversely, if K is less than one, the protein unfolds at a slower rate than it folds, and its Gibbs energy is positive. Also, K is equal to the ratio of the concentration of protein in the unfolded state and the concentration of protein in the folded state K=[U]/[F].

In addition, it has been observed that, for chemical denaturants, a nearly linear relationship exists between the Gibbs energy and the concentration of the denaturant. This relationship may be expressed as $$\Delta G = \Delta G_0 - m^*[\text{denaturant}],$$

where $\Delta G_0$ is the intrinsic Gibbs energy, [denaturant] is the concentration of denaturant, and m is the multiplier, which is unique for a particular protein.

For a native/unfolded equilibrium, the fraction of protein molecules which are unfolded, or denatured, $F_d$, is given by:

$$F_d = \frac{K}{1+K},$$

where K is the equilibrium constant.

This equation can be used to allow calculation of a denaturation curve. When a protein changes from its folded state to an unfolded state, certain measurable characteristics of the protein also change. One such characteristic is the fluorescence of the protein.

While the preferred embodiment described in this application utilizes fluorescence emission (intrinsic or extrinsic) as a way to determine the degree of denaturation or unfolding of a protein, the disclosure is not limited to this technique. There are many physical observable properties and their associated instrumentation, in addition to fluorescence spectroscopy, that are sensitive to the degree of denaturation of a protein. These observable properties include, but are not limited to uv/vis spectroscopy, circular dichroism, nuclear magnetic resonance (NMR), infrared spectroscopy (IR) among others.

Figure 1:
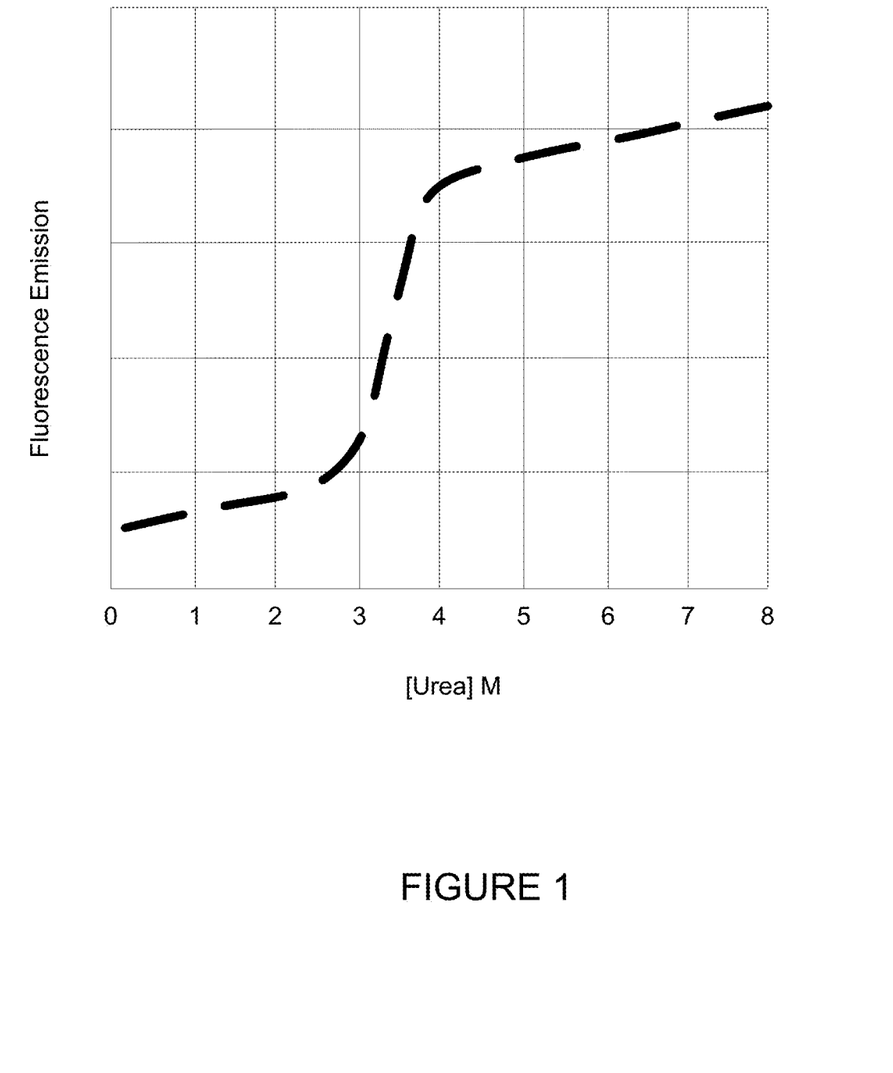
FIG. 1 is a denaturation graph of the prior art.

FIG. 1 shows a typical urea denaturation curve for an antibody. The y, or vertical, axis is a measure of the intrinsic fluorescence of the protein. The fluorescence of different dyes, usually known as protein probes, can also be used. The horizontal, or x, axis is the concentration of urea in solution with the protein. As can be seen, at a certain point, between 3M and 4M urea, the fluorescence of the protein changes dramatically, indicating that it has denatured.

The generation of the data needed to produce such a graph is laborious. In one scenario, a solution containing the protein and any excipients is prepared. A sample of this solution is then subjected to fluorescent light and the emission is recorded. This is the baseline fluorescence with no chemical denaturant. In some embodiments, an amount of urea is then added to the remainder of the solution, and the light test is repeated on a portion of this modified solution. An additional amount of urea is then added to the remainder of the solution and a third light test is performed. This process is repeated for the number of desired samples. The amount of urea added each time is a function of the desired granularity of the test, and the range of urea molarities to be included. Such a method is prone to errors, as there are cumulative errors due to the constant addition of urea to the remaining solution. In this stepwise urea addition method, the process will result in the dilution of the protein and also a smaller fluorescence signal. In addition, since the solubility of urea is about 10.5M and a final 8M urea concentration is needed, the starting protein solution volume needs to be extremely small. The protein will be significantly diluted as the experiment progresses.

In another embodiment, a plurality of solutions, each with the protein, any excipients, and the proper amount of urea, is individually prepared. Each of these prepared solutions is then light tested to determine its fluorescence. While this method removes the cumulative errors associated with the previous method, it is extremely time consuming, especially for a large number of samples.

The resulting denaturation graph shows the stability of a particular combination of buffer, ligand and excipient conditions in the presence of a chemical denaturant. More stable combinations have a similarly shaped graph, shifted to the right. Conversely, less stable combinations have a graph shifted to the left. The goal of this testing is to find a combination with the maximum stability in the presence of the chemical denaturant. This combination can then be used as the storage formulation for the protein as it is stored and shipped.

Given the increased importance of developing proteins for pharmaceutical purposes, there is a dearth of systems and methods available to aid in the determination of the ideal storage formulation in which the protein is most stable.

For example, one important parameter that affects protein stability is pH. However, there are no known methods to create a buffer solution having a specific pH, which can then be used for denaturation testing. Furthermore, there are no automated methods that can be used to accurately achieve a plurality of buffer solutions, each having a desired pH, such as for use in a denaturation test, without the need to measure the pH for each solution.

SUMMARY OF THE INVENTION

A system and method for automatically creating a buffer solution having a desired pH value is disclosed. In accordance with certain embodiments, the method uses two known buffer solutions, each with predetermined or known pH values, and determines a mathematical relationship which defines the amount of each known buffer solution needed to create the buffer solution with the desired pH. This method can then be used to create one or more denaturation graphs, which demonstrate the stability of a protein at a given pH level.

DETAILED DESCRIPTION OF THE INVENTION

FIG. 1 shows a typical denaturation graph, used to determine the stability of a protein in the presence of a chemical denaturant. This graph shows the stability of the protein for a particular combination of buffer, ligand and excipients conditions. However, it is often useful to view a plurality of these graphs to understand how changes in the buffer, ligand or excipients affects the stability of the protein.

For example, for a particular combination, it may be of interest to understand how various concentrations of a compound, such as a salt, pH, excipients, or ligands may affect the stability of the protein. For example, it may be of interest to measure the effects of different concentrations of salt in combination with a particular buffer and ligand. To do this, one may create four different formulations:

Formulation 1: solution with minimum salt and no denaturant
Formulation 2: solution with minimum salt and maximum denaturant
Formulation 3: solution with maximum salt and no denaturant
Formulation 4: solution with maximum salt and maximum denaturant While the descriptions in this disclosure refer to certain formulations having no denaturant, it is understood that, in another embodiment, Formulations 1 and 3 contain a minimum amount of denaturant, which may be greater than 0, while Formulations 2 and 4 contain a maximum amount of denaturant.

To create a denaturation graph, one may begin by using only formulations 1 and 2. By combining these two formulations in different proportions, one can create a plurality of solutions, each with a minimum amount of salt and a varying amount of chemical denaturant. This plurality of solutions can be used to create a first denaturant graph.

Similarly, formulations 3 and 4 can be used to create a second denaturation graph, showing the stability of a solution with a maximum amount of salt with varying amounts of chemical denaturant.

A set of other graphs can also be created, each of which has a salt concentration between the minimum and maximum values. The particular number of graphs within the set is not particularly limited, and can be predetermined or arbitrary. For example, a denaturation graph showing the effect of chemical denaturant, with a salt concentration that is the average of the minimum and maximum values, may be created. In this scenario, a new formulation is created by mixing Formulation 1 and Formulation 3 in equal amounts. This new formulation has a salt concentration exactly halfway between the minimum and maximum values, with no chemical denaturant. Similarly, a second new formulation is created by mixing equal amounts of Formulation 2 and Formulation 4. This new formulation has a salt concentration exactly halfway between the minimum and maximum values, with a maximum amount of chemical denaturant. The denaturant graph for this salt concentration is then created as described above.

Figure 2:
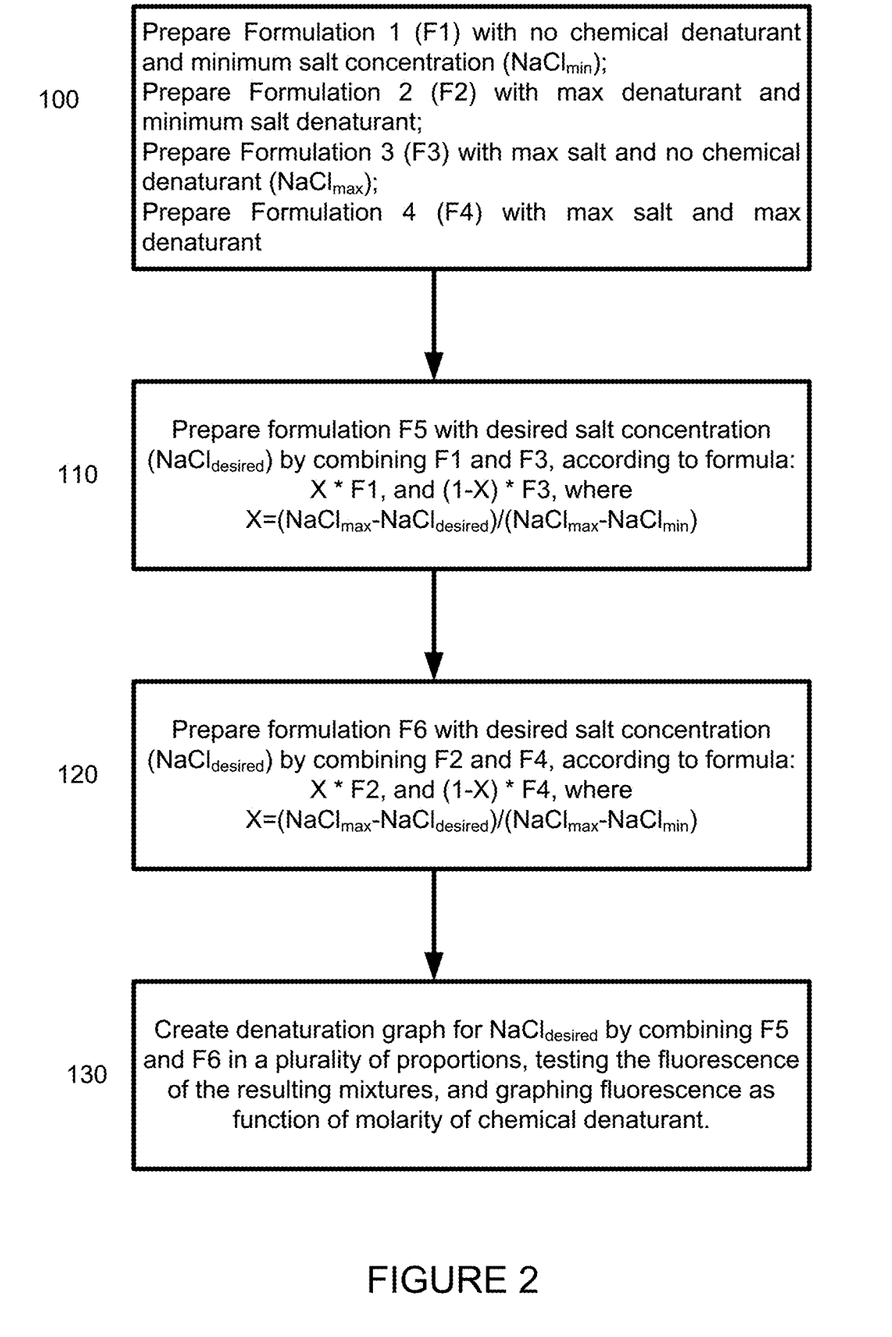
FIG. 2 is a flowchart illustrating a process to generate a denaturation graph with a desired salt concentration.

This process can be repeated a plurality of times to create the required or desired granularity of salt concentration. FIG. 2 shows a flowchart showing this sequence. In step 100, the four formulations, labeled F1 through F4, are prepared. These four formulations represent the four corners of the testing. In step 110, a fifth formulation, which has the desired amount of salt and no chemical denaturant, is prepared, using the equation shown. This equation assumes a linear relationship and is used to create any desired concentration between the minimum salt concentration and the maximum salt concentration. Similarly, in step 120, a sixth formulation, which has the desired amount of salt and the maximum amount of chemical denaturant is prepared, using the equation shown. It should be noted that the fifth and sixth concentrations may each be prepared in a separate well or vessel, so as to be available for future use. However, in other embodiments, the fifth and sixth formulations need not be independently created. Rather, the formulations F1, F2, F3 and F4 may be combined in the specific ratios described by these equations in a single well or vessel, without the intermediate formulations F5, F6 being prepared in a separate vessel. Thus, the terms "fifth formulation" and "sixth formulation" are used to express the ratios of F1 and F3, and F2 and F4, respectively, even in the scenario where such formulations may not exist in an isolated vessel. Finally, as shown in step 130, using the fifth and sixth formulations, a denaturation graph can be prepared. For an eleven point graph, the F5 and F6 formulations may be combined as shown in Table 1 below.

TABLE 1

| Point Number | % of F5 | % of F6 |
|---|---|---|
| 1 | 100 | 0 |
| 2 | 90 | 10 |
| 3 | 80 | 20 |
| 4 | 70 | 30 |
| 5 | 60 | 40 |
| 6 | 50 | 50 |
| 7 | 40 | 60 |
| 8 | 30 | 70 |
| 9 | 20 | 80 |
| 10 | 10 | 90 |
| 11 | 0 | 100 |

Each of these points is prepared and then subjected to testing, where the observable property is measured. In one embodiment, this testing includes the measurement of the fluorescence emission of the protein itself (intrinsic) or a fluorescence probe that is sensitive to protein denaturation after being excited with a light of a wavelength that is absorbed by the protein or fluorescence probe. The fluorescence of each data point is measured and recorded. The fluorescence is then plotted as a function of the molarity of the chemical denaturant. The result of this process is a denaturation graph. The process shown in FIG. 2 can be repeated for an arbitrary number of salt concentrations.

Certain elements, such as salt, can be mixed according to linear models, using the equations shown in steps 110 and 120 of FIG. 2.

However, other parameters cannot be calculated linearly. One such important parameter is pH. For example, if equal parts of a base solution with a pH of 10 is mixed with an acid having a pH of 4, the resulting mixture does not necessarily have a pH of 7. Thus, the process shown in FIG. 2 to create a plurality of denaturation graphs cannot be used with consistent reliability for characterization of the effect of pH on protein stability.

In one embodiment, an acidic solution, having a pH of 4, is created. The solution may contain L-histidine and is made acidic through the introduction of one or more acids, such as succinic acid and/or phosphoric acid. If necessary, the pH can be increased through the introduction of NaOH. A basic solution, having a pH of 9, is also created using L-histidine. In this case, $Na_2HPO_4$ is used to make the solution basic. If necessary, the pH can be further increased through the introduction of NaOH.

Figure 3:
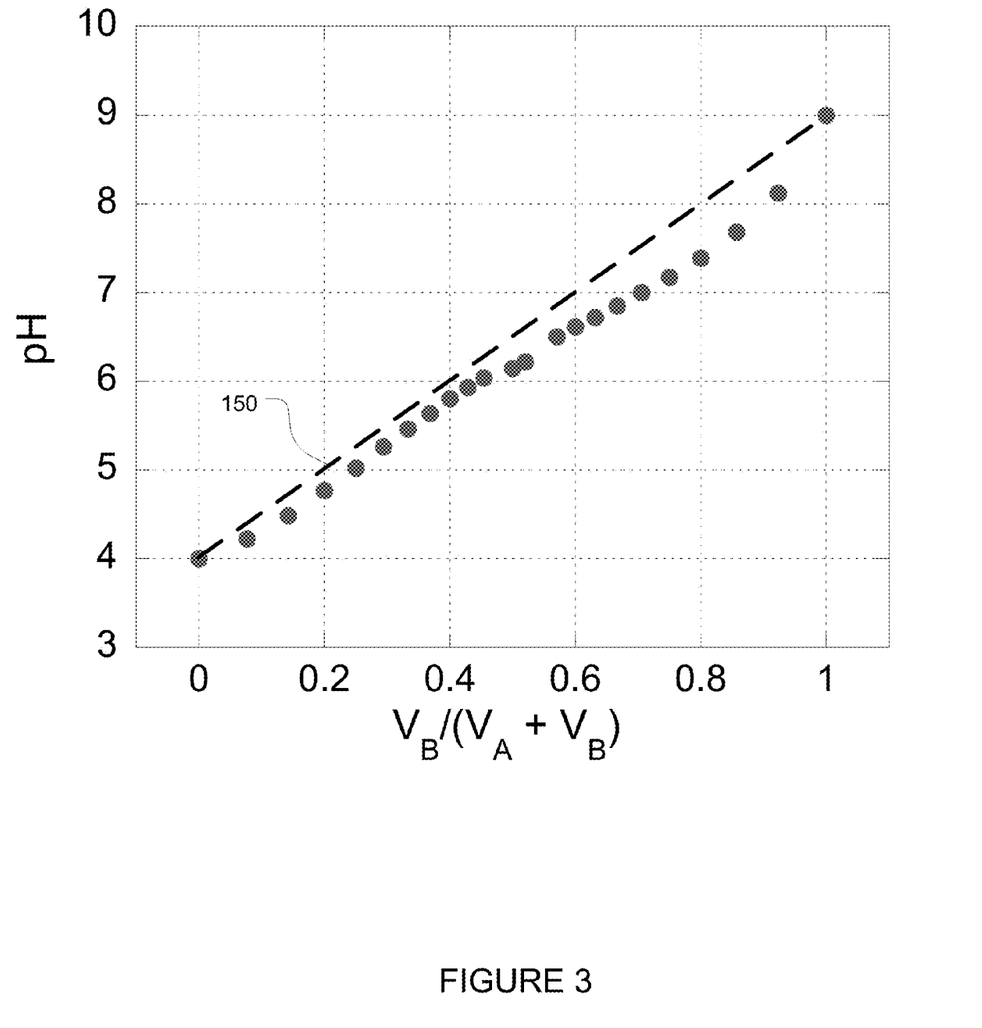
FIG. 3 is a graph showing the relationship between Fraction Basic and pH for a particular buffer.

In one embodiment, these two solutions are mixed in a plurality of combinations, and the pH of each resulting mixture is measured. FIG. 3 shows the actual measured pH for these solutions. The x, or horizontal, axis is the fraction of the resulting mixture which is the base, also referred to as Fraction Basic ($F_B$), expressed as $$\frac{V_B}{V_A + V_B},$$

where $V_B$ is the volume of basic solution and $V_A$ is the volume of acidic solution. The y, or vertical, axis represents the pH of the mixture. The points on the graph represent actual measured pH values, while broken line 150 is used to show a theoretical linear relationship between x and y from the pH 4 solution to the pH 9 solution. As can be readily seen, a linear relationship, such as that used in FIG. 2, is not an accurate representation of the pH relationship. Thus, the method and equations described in conjunction with FIG. 2 will not produce accurate results.

It should be noted that FIG. 3 shows the pH of mixtures of two solutions. Different curves may be obtained if L-histidine is replaced with a different protein stabilizing inducing ligand.

Figure 4A:
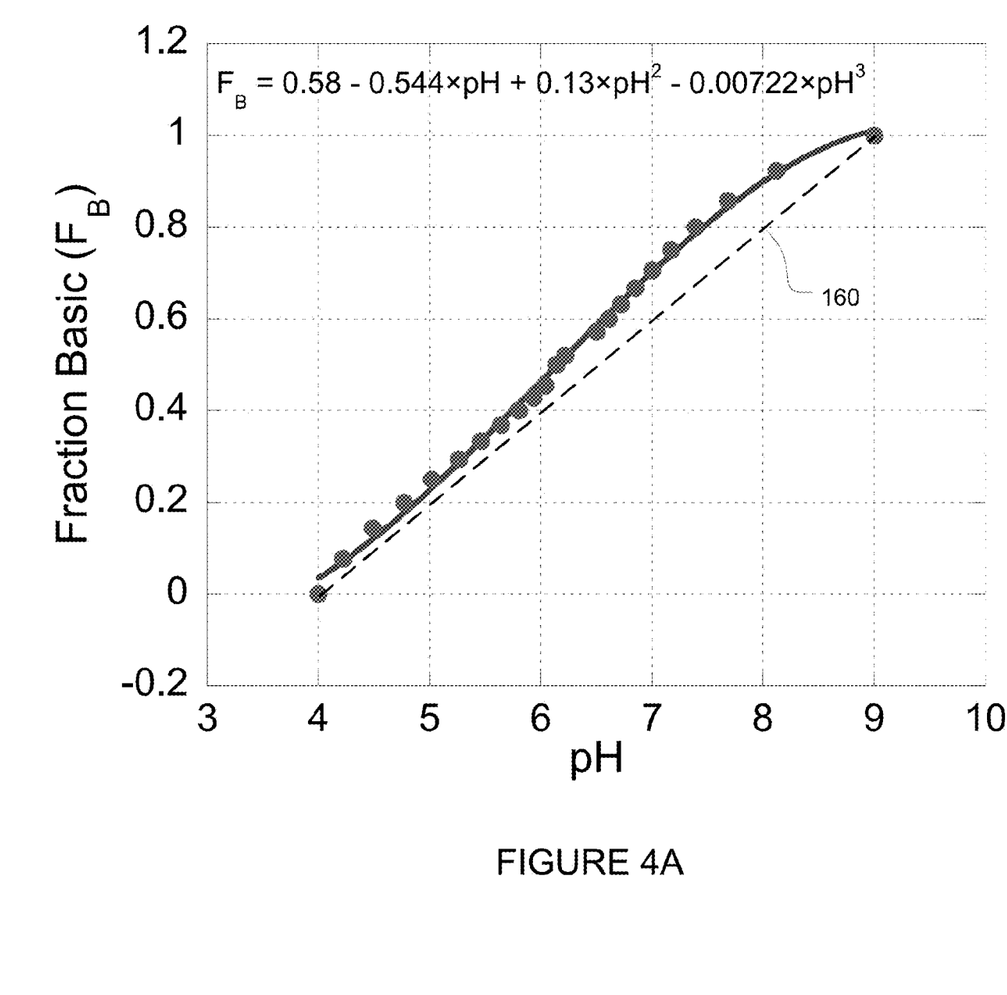
FIG. 4A is the inverse of FIG. 3.

Of more interest is the inverse of this graph. In other words, it would be useful to know the required Fraction Basic ($F_B$) for a desired pH. FIG. 4A shows the graph of Fraction Basic ($F_B$) as a function of pH. This is obtained by simply reversing the coordinates of each point on the graph shown in FIG. 3. Line 160 again is drawn to show a theoretical linear relationship between Fraction Basic ($F_B$) and pH, from the pH 4 solution to the pH 9 solution.

Using the points shown on the graph of FIG. 4A, a non-linear best fit line can be drawn. In some embodiments, a best fit cubic equation is generated. For example, in the example shown in FIGS. 3 and 4A, the best fit cubic equation is given by:

$$F_B = 0.58 - 0.544*pH + 0.13*pH^2 - 0.00722*pH^3$$

Figure 4B:
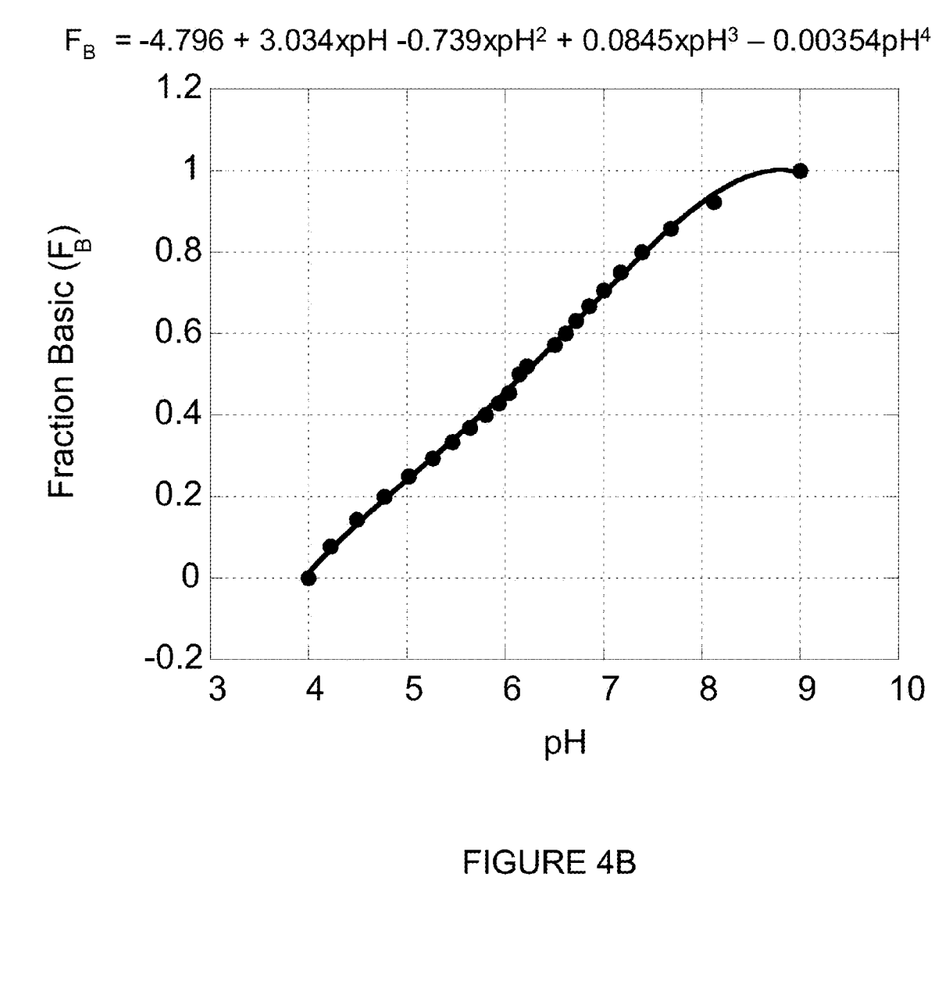
FIG. 4B is a best fit fourth order equation.

In another embodiment, a higher order best fit equation is generated, such as a fourth or fifth order equation. FIG. 4B shows a best fit fourth order equation, given by the formula:

$$F_B = -4.796 + 3.034*pH - 0.739*pH^2 + 0.0845*pH^3 - 0.00354*pH^4$$

Figure 4C:
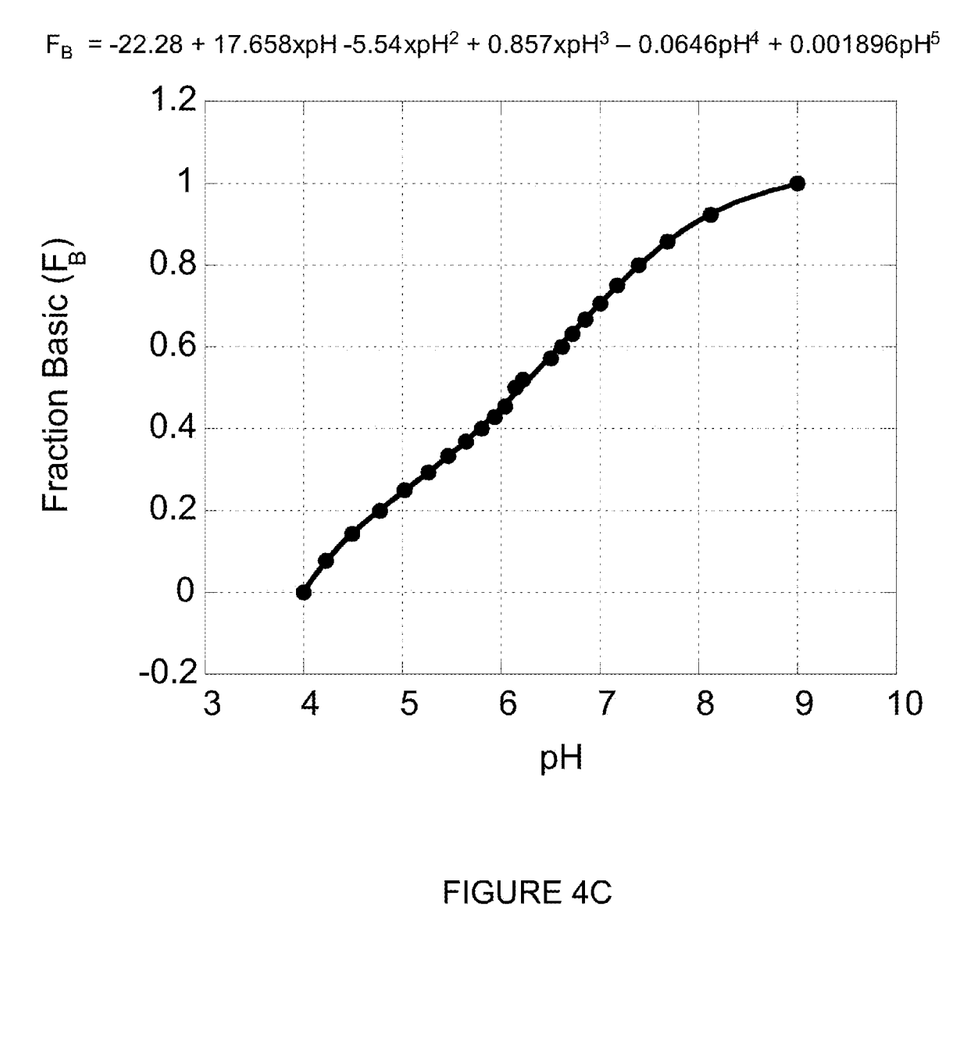
FIG. 4C is a best fit fifth order equation.

FIG. 4C shows a best fit fifth order equation, given by the formula:

$$F_B = 22.28 + 17.658*pH - 5.54*pH^2 + 0.857*pH^3 - 0.0646*pH^4 + 0.001896*pH^5$$

The use of a higher order best fit equation allows for an accurate relationship between pH and Fraction Basic over a wide range of pH values, such as between 3 and 9, or even wider. Thus, a non-linear mathematical relationship can be used to determine the appropriate ratios of acid and base to create a buffer of any desired pH value for a given ligand.

Figure 5:
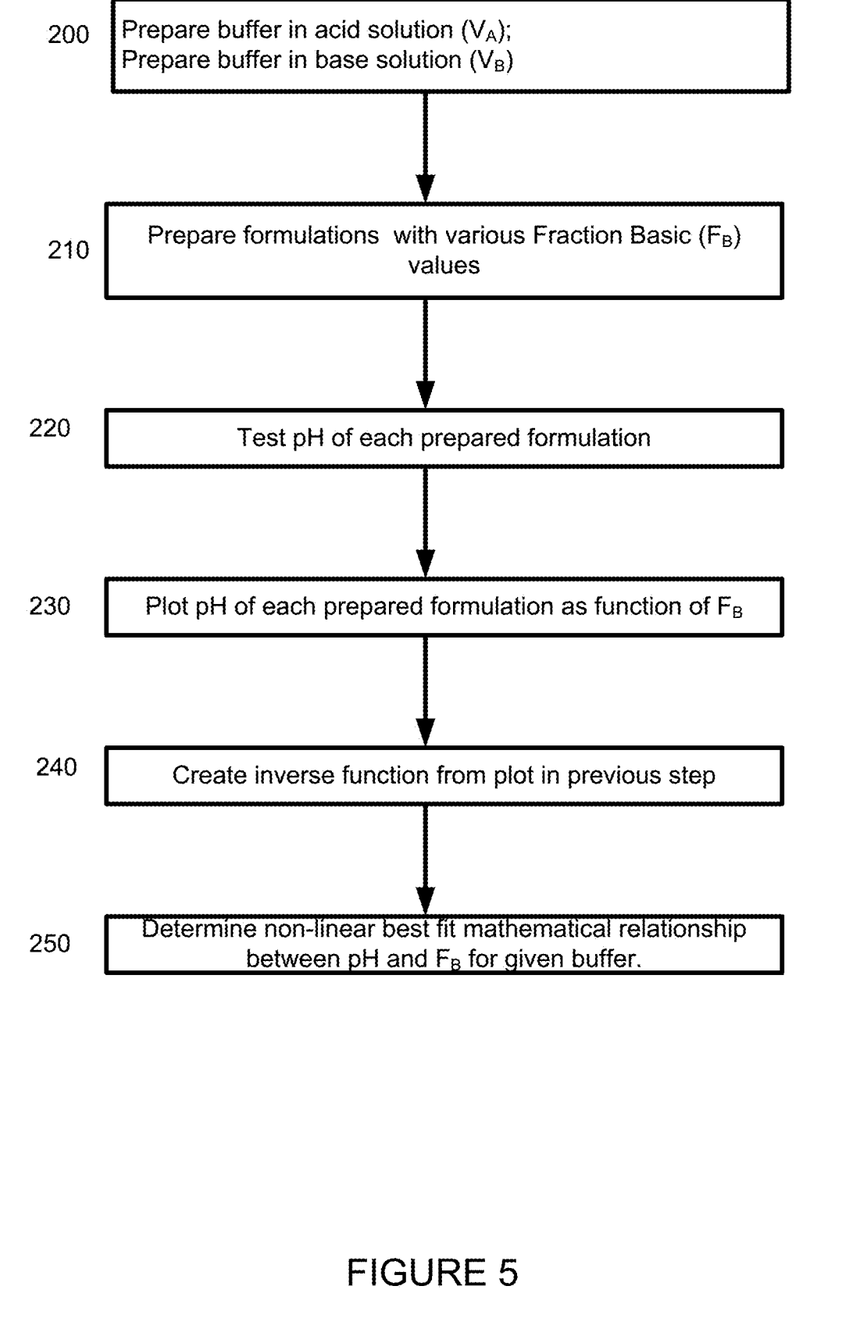
FIG. 5 is a flowchart illustrating a process to determine the non-linear best fit relationship between pH and Fraction Basic for a particular buffer.

FIG. 5 represents a simplified flowchart of this operation. In step 200, the buffer is prepared in two solutions, one acidic having a first pH, and one basic, having a second, higher pH. The two pH values can be any values, such as 3 and 9, or other ranges. In step 210, a plurality of formulations is prepared, each with a unique Fraction Basic ($F_B$). In one embodiment, formulations having twenty or more unique $F_B$ values are created. Each of these formulations is then tested to determine its pH, as shown in step 220. The results of this test are plotted, as shown in step 230. The inverse function, which shows $F_B$ as a function of pH, is then created, as shown in step 240. It should be noted that the function created in step 240 can be generated directly from the data generated in step 220. Once the points have been determined, a computer tool, or other method, may be used to determine the best non-linear best fit mathematical relationship between pH and $F_B$ for this buffer, as shown in step 250. In some embodiments, a cubic equation is generated, although other order polynomials may also be used.

Figure 6:
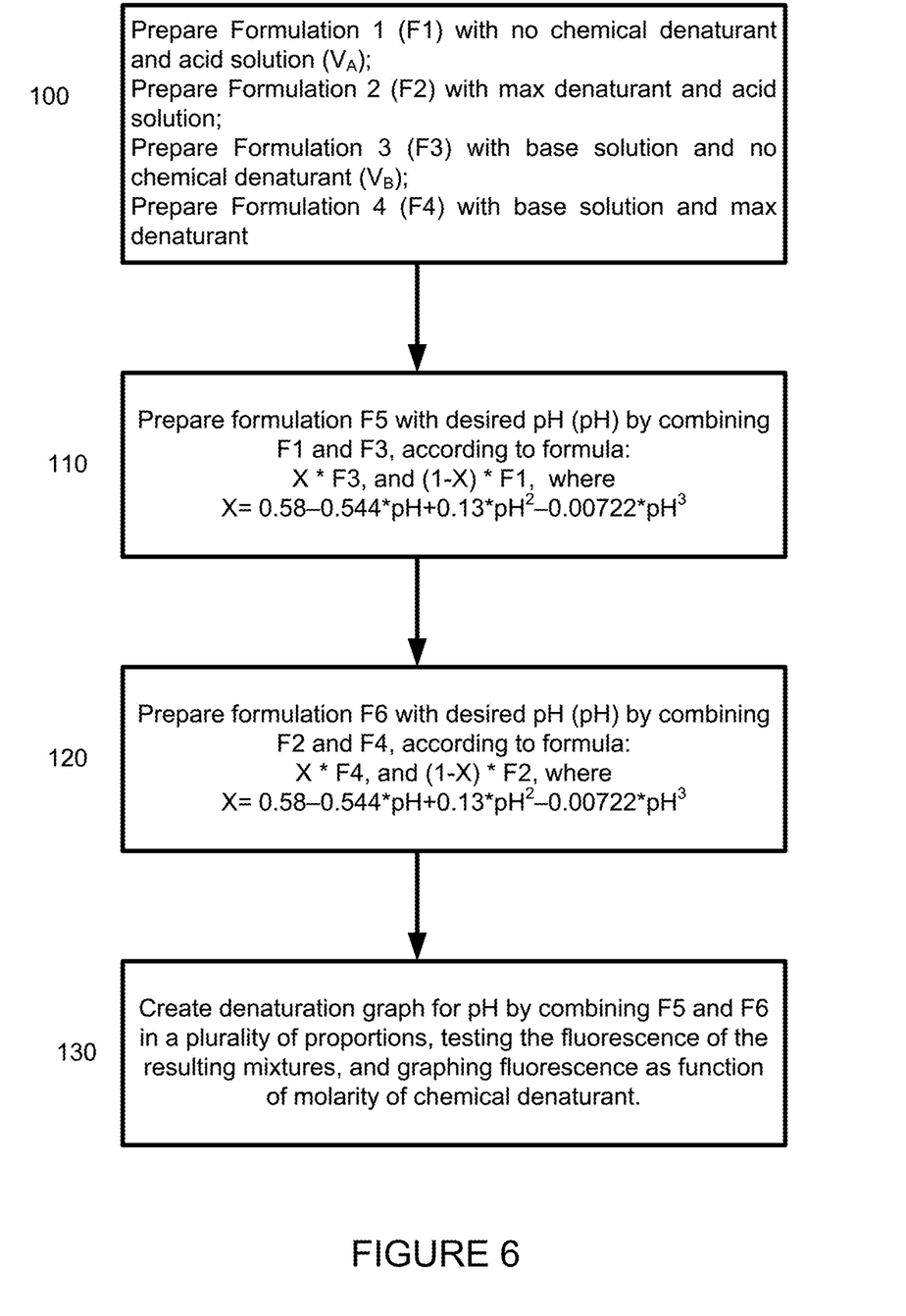
FIG. 6 is a flowchart illustrating a process to generate a denaturation graph with a desired pH.

Once this equation has been generated, the process of creating a plurality of different denaturation graphs, each with common buffer and ligand, and a different pH, can be completed. FIG. 6 shows a modified version of the flowchart of FIG. 2, which can be used to generate denaturation graphs for a plurality of pH values. Thus, this method allows the creation of a buffer of any desired pH simply by mixing two solutions of different pH values in appropriate proportions, as determined by a non-linear mathematical relationship, such as a cubic equation. It should be noted that the fifth and sixth concentrations F5, F6, respectively, can each be prepared in a separate well or vessel, so as to be available for future use. However, in other embodiments, the fifth and sixth formulations may not be independently created. Rather, the formulations F1, F2, F3 and F4 may be combined in the specific ratios described by these equations in a single well or vessel, without the intermediate formulations F5, F6 being prepared in a separate vessel. Thus, the terms "fifth formulation" and "sixth formulation" are used to express the ratios of F1 and F3, and F2 and F4, respectively, even in the scenario where such formulations may not exist in an isolated vessel. This method is ideally suited for automatic generation of buffer solutions of specified pH values It is believed that buffer solution containing different ingredients will generate somewhat different mathematical relationships. Therefore, it may be necessary to perform the method described in FIGS. 3-5 for each set of ingredients to determine its best fit equation. However, once generated, these equations are applicable to denaturation testing for any protein.

Figure 7:
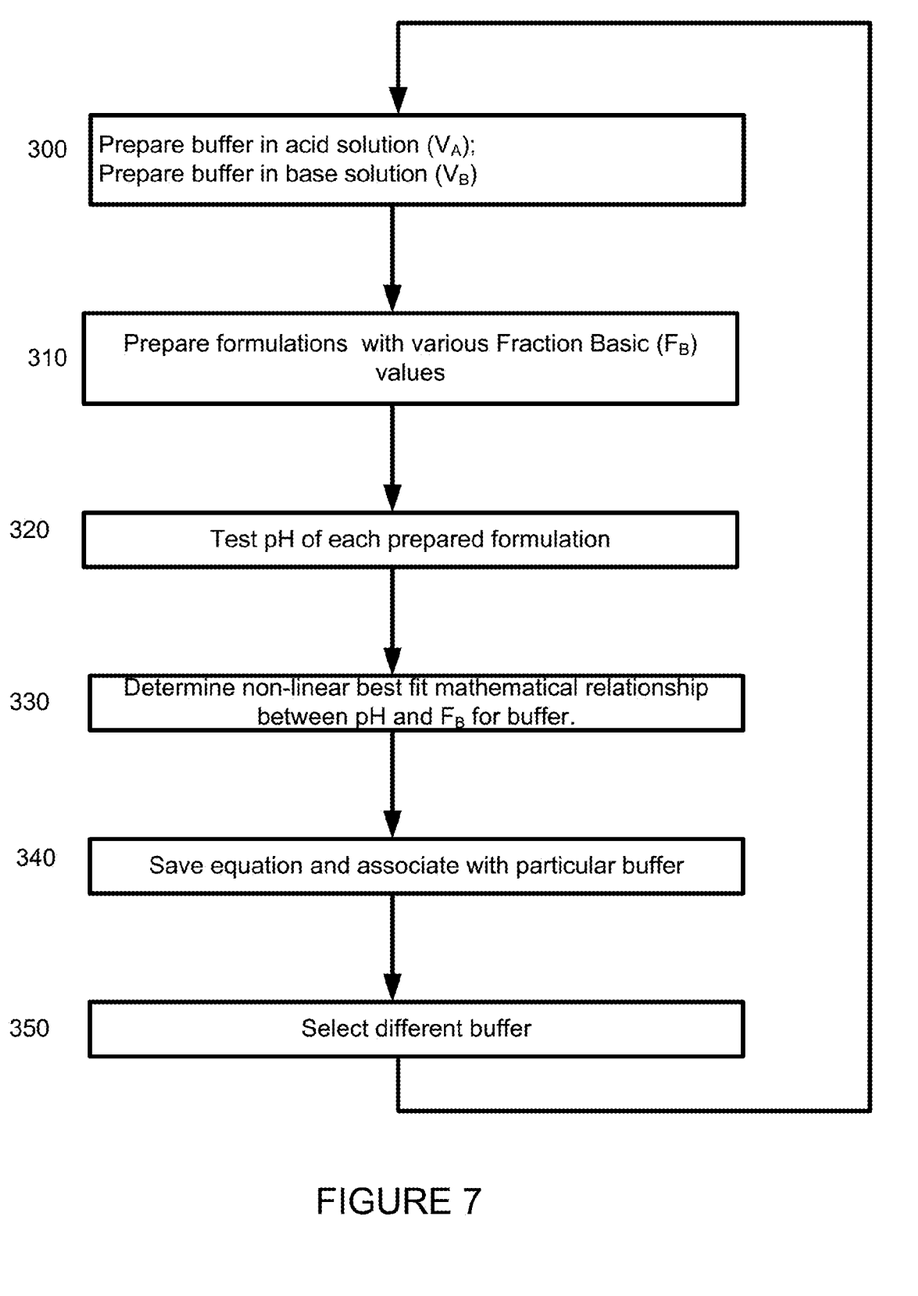
FIG. 7 is a flowchart illustrating a process to create a library of predetermined best fit equations for a plurality of buffers.

FIG. 7 shows a method that is used to create a library of buffers, which can then be used to create a plurality of denaturation graphs for any protein. A first buffer is prepared in acid and base solutions, as shown in step 300. As described above, formulations having various Fraction Basic values are prepared, as shown in step 310. Each formulation is pH test (step 320) and based on this, the non-linear best fit mathematical relationship is determined for this particular ligand, as shown in step 340. This equation is then saved, and associated with the particular buffer, such as in a database or other computer storage medium, as shown in step 340. Finally, a different buffer is selected (step 350) and this process is repeated. This process can be performed for as many buffers as desired.

The generation of a table or database of buffers, and corresponding non-linear best fit equations can be used to determine the best buffer to use with a particular protein. After a particular protein has been identified as suitable for a pharmaceutical purpose, it may be advantageous to determine the pH and buffer in which the protein is most stable. The operator may select a first buffer, which has been previously characterized such that a pre-determined non-linear best fit mathematical relationship exists. The operator may then select the desired range of pH values that are desired to be tested, as well as the division or step size. Then, by repeated execution of the flowchart shown in FIG. 6, a set of denaturation graphs is generated for the selected buffer, where each graph represents a specific pH value within the range requested by the operator.

After this set of tests is completed, the operator may select a second buffer, which has been previously characterized such that a pre-determined non-linear best fit mathematical relationship exists. The procedure detailed above is then repeated for this second buffer. This process can be repeated for as many buffers as desired.

In one embodiment, the processes described herein may be automated. In this embodiment, an apparatus having a controller with a processing unit and a storage element is used. The storage element may be RAM, DRAM, ROM, Flash ROM, EEROM, magnetic media, or any other medium suitable to hold computer readable data and instructions. The instructions may be those necessary to execute the flowchart of FIG. 2, FIG. 5 or FIG. 6. The processing unit may be a dedicated microcontroller, a personal computer or any other suitable computing device. In addition, the apparatus has a pump or siphon system, which allows cannulas to extract liquid from a first well (F1), a second well (F2), a third well (F3) and a fourth well (F4) in exact quantities and mix these liquids together, preferably in another well. The apparatus also includes one or more actuators, which can move the cannulas from one position to another, so as to draw fluid from a first well and expel the fluid into a second well. In this embodiment, the operator may enter the identity of the buffer that is desired. The equipment, in its storage element, may have a mapping which correlates the selected buffer with the non-linear equation to be used. The operator then enters the pH minimum, pH maximum and pH step size. In another embodiment, the operator enters the coefficients of the non-linear best fit equation.

As stated above, in some embodiments, the generation of the non-linear mathematical relationship is generated automatically. To execute the flowchart of FIG. 5, the controller may be in communication with a pH indicator. This is so that after using the above described equipment to create formulations with various Fraction Basic values, the pH indicator may provide pH information to the controller, as shown in steps 230 and 240. In addition, the controller may also have a software application that creates a non-linear best fit mathematical relationship based on the Fraction Basic values and the measured pH values. Using the resulting best fit mathematical relationship, a formulation having any desired pH can be created.

Based on the entered parameters, the controller executed a series of instructions or steps. The coefficients of the non-linear best fit equation are selected, which allows the controller to determine Fraction Basic for a given pH. Then, the pH to be tested is determined. For the first test, this is equal to the pH minimum entered by the operator.

For each pH, the controller, using the flowchart of FIG. 6, creates a denaturation curve. This data can be output, such as on a display device or printer. In some embodiments, this graph is stored in the storage element of the apparatus.

For each subsequent test, the new pH to be tested is equal to pH min+pH step size*(test number−1). In other words, the new pH to be tested is equal to the pH that was previously tested+pH step size. Using this new pH value, a new Fraction Basic is determined, and the process of FIG. 6 is repeated. This process is repeated until the pH to be tested is greater than the pH maximum entered by the operator. At this point, the pH testing for the selected buffer has been completed.

The operator may then enter a different buffer to be tested and enter the required parameters to the apparatus and repeat the processes described above. This automation allows the operator to quickly and accurately measure the effect of pH on the stability of a protein in a particular buffer solution. It also allows rapid comparison of different buffer solutions, as described above.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

What is claimed is:

1. A method of creating a denaturizing graph for a buffer at a desired pH, comprising:
    providing a first solution with a first pH and a predetermined minimum amount of chemical denaturant, a second solution having said first pH and a predetermined maximum amount of a chemical denaturant, a third solution having a second pH and a predetermined minimum amount of chemical denaturant, and a fourth solution having said second pH and said predetermined maximum amount of said chemical denaturant;
    using a combining method to combine said first solution and said third solution into a fifth solution having said desired pH and a predetermined minimum amount of chemical denaturant;
    using the combining method to combine said second solution and said fourth solution into a sixth solution having said desired pH and said maximum amount of chemical denaturant;
    mixing said fifth and sixth solution in a plurality of samples, each having said fifth and sixth solution in different proportions to create solutions having said desired pH and different molarities of said chemical denaturant;
    measuring an observable property of each of said plurality of samples; and
    creating a denaturation graph based on said observable property and said molarity, wherein the combining method comprises:
        preparing a plurality of formulations, based on two solutions, each formulation having different fractions of the two solutions;
        determining the pH of each of said formulations;
        recording each of said fractions and said determined pH values;
        determining a non-linear best fit mathematical relationship between said fractions and said pH;
        entering desired pH value into said non-linear mathematical relationship to determine a fraction of each of the two solutions to be used to achieve said desired pH; and
        preparing said buffer of said desired pH using said determined fractions.

2. The method of claim 1, wherein said observable property comprises fluorescence.

3. The method of claim 1, wherein said fifth solution and sixth solution are created in respective containers.

4. The method of claim 1, wherein said chemical denaturant comprises urea.

5. The method of claim 1, wherein said predetermined minimum amount of denaturant comprises no denaturant.

* * * * *

UNITED STATES PATENT AND TRADEMARK OFFICE
CERTIFICATE OF CORRECTION

PATENT NO.       : 9,606,061 B2                                              Page 1 of 1
APPLICATION NO. : 14/709666
DATED            : March 28, 2017
INVENTOR(S)      : Brown et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 87 days.

Signed and Sealed this
Twenty-fifth Day of September, 2018

Andrei Iancu
*Director of the United States Patent and Trademark Office*